United States Patent [19]

Andreas

[11] 4,270,533

[45] Jun. 2, 1981

[54] MULTIPLE CHAMBER CONTAINER FOR DELIVERING LIQUID UNDER PRESSURE

[76] Inventor: Joseph M. Andreas, Two Maple Ter., Newbury, Mass. 01950

[21] Appl. No.: 825,143

[22] Filed: Aug. 16, 1977

[51] Int. Cl.³ .............................................. A61M 5/00
[52] U.S. Cl. ............................ 128/214 F; 128/214 D; 128/DIG. 12; 150/2.5; 222/95
[58] Field of Search ........... 128/214 R, 214 D, 214 F, 128/227, DIG. 12, 272; 222/94, 95, 105; 150/2.5

[56] References Cited

U.S. PATENT DOCUMENTS

| | | | |
|---|---|---|---|
| 2,766,907 | 10/1956 | Wallace | 222/94 |
| 3,054,401 | 9/1962 | Gewecke | 128/214 F |
| 3,228,395 | 1/1966 | Gewecke | 128/214 F |
| 3,335,912 | 8/1967 | Reeves | 222/94 |
| 3,888,239 | 6/1975 | Rubinstein | 128/214 F X |

FOREIGN PATENT DOCUMENTS 2006054  8/1971  Fed. Rep. of Germany ....... 128/214 F

*Primary Examiner*—Dalton L. Truluck

*Attorney, Agent, or Firm*—Cesari & McKenna

[57] ABSTRACT

An improved flexible-walled, bag-type container of the kind used for the storage of parenteral fluids such as saline solutions and blood, and for the administration of these fluids to patients under pressure. The container is characterized in one embodiment by relatively heavy gauge exterior walls formed of two bonded flexible sheets and an additional flexible interior wall of relatively light gauge. One peripheral portion of this additional wall member is bonded to an intermediate portion of one exterior wall and the remaining portions of the flexible wall member, that are co-extensive with the outer peripheral portions of the exterior walls, are bonded together. The container then has a first chamber for the liquid and a second chamber that can be expanded by means of an external pumping apparatus for forcing the liquid from the first chamber under pressure through a conduit. In another embodiment, a second interior wall is formed and the space between the first and second interior walls is vented to the atmosphere thereby to prevent the passage of any gas from the second chamber into the first chamber.

10 Claims, 7 Drawing Figures

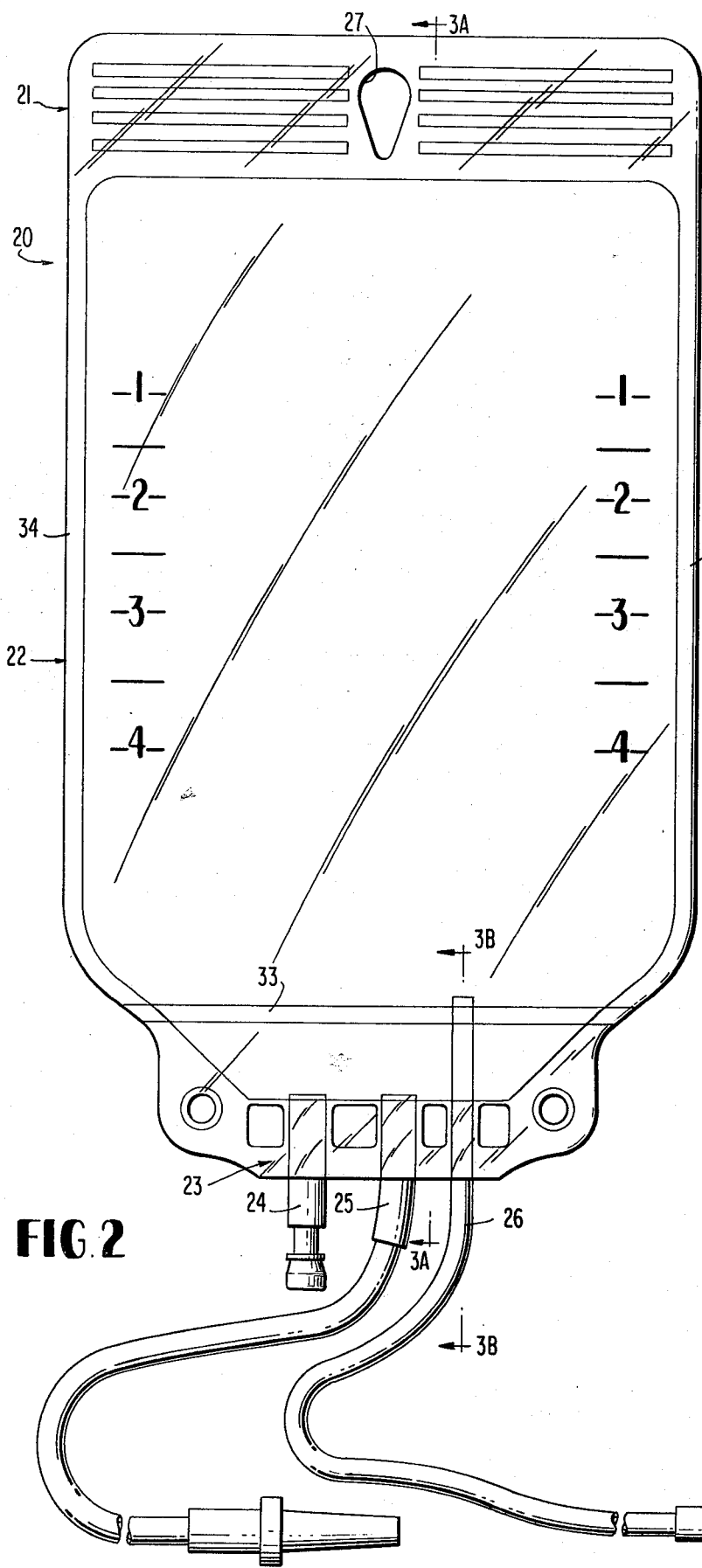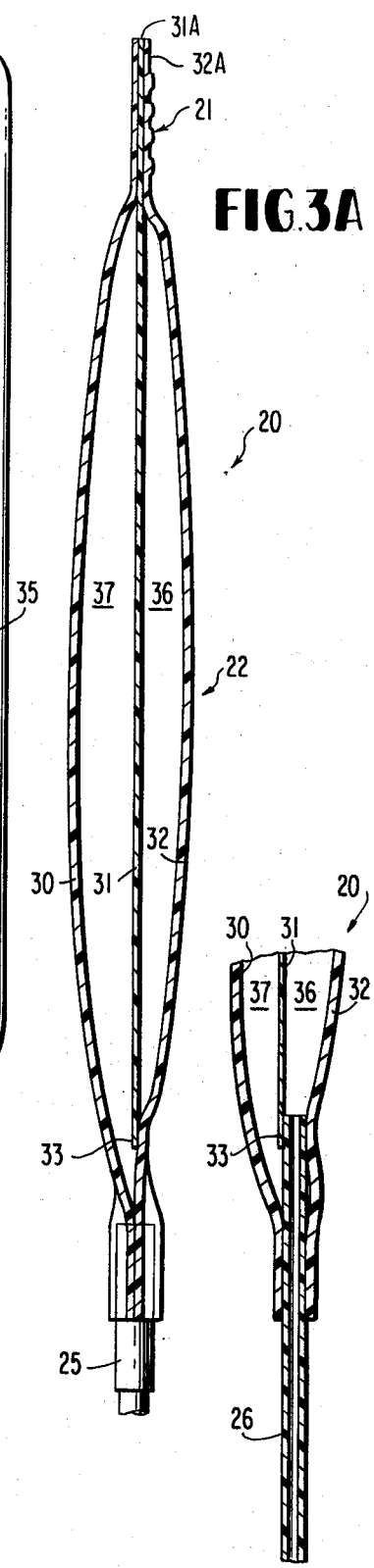
FIG.2
FIG.3A
FIG.3B

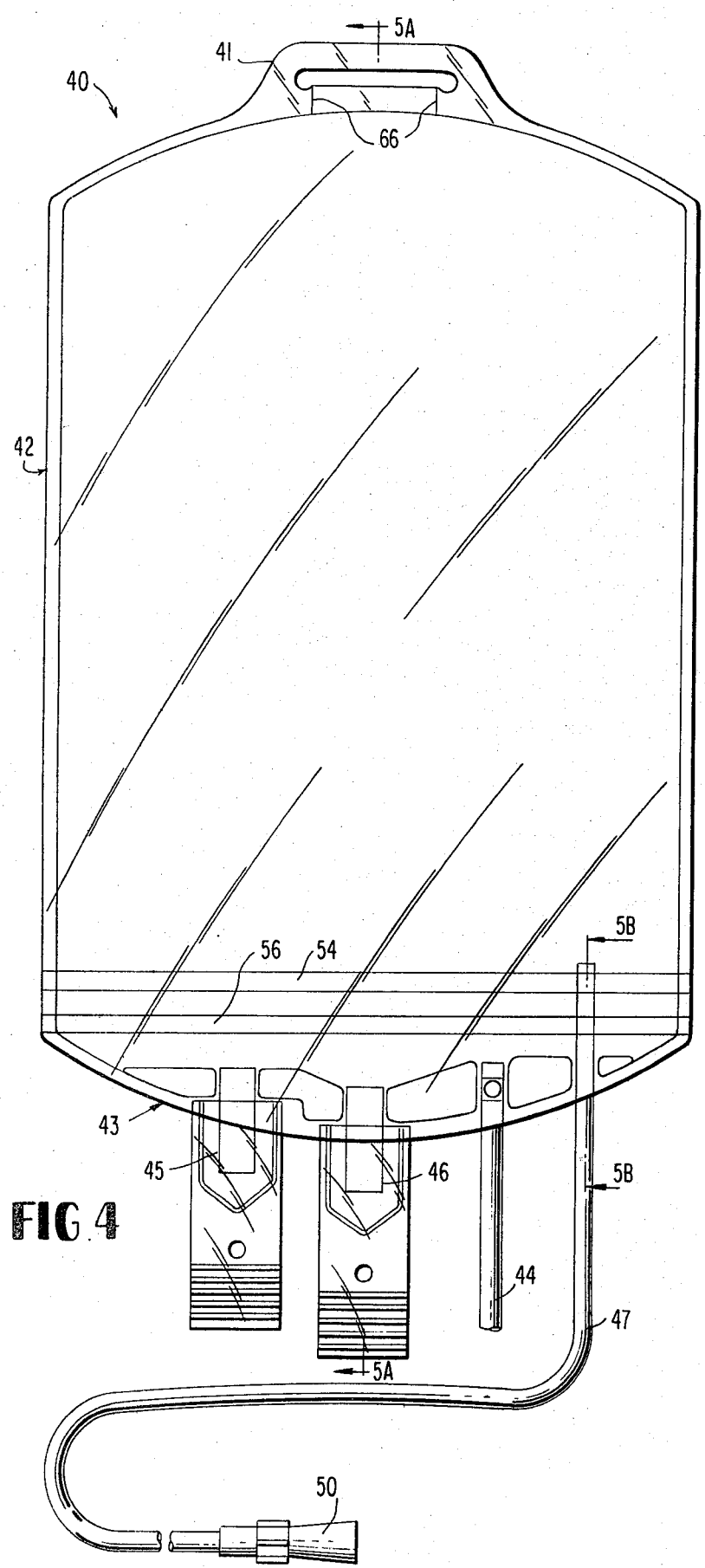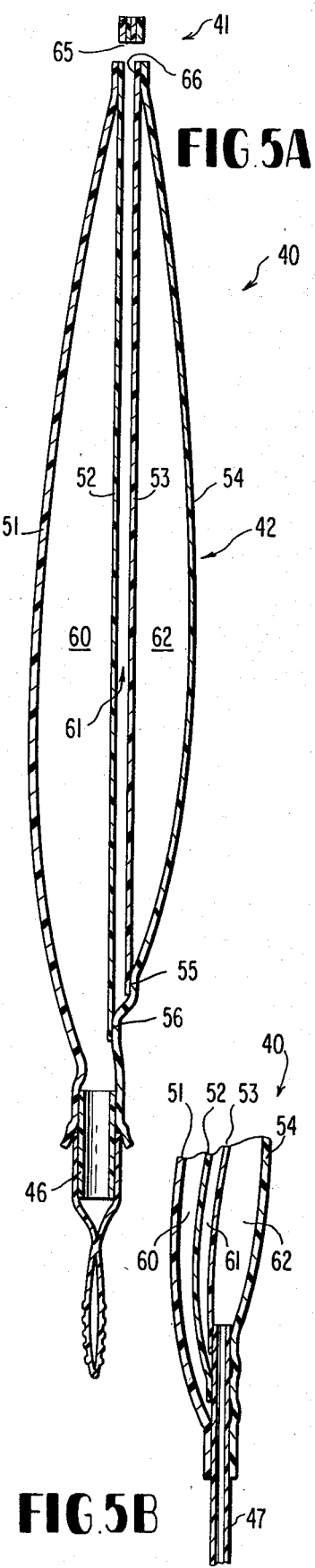

MULTIPLE CHAMBER CONTAINER FOR DELIVERING LIQUID UNDER PRESSURE

BACKGROUND OF THE INVENTION

This invention generally relates to medicators for use in surgical and related procedures and more specifically to apparatus for the administration of beneficial parenteral liquids, such as blood, saline solutions and the like.

These liquids are sometimes stored in glass bottles. To administer such liquids, the bottle is placed above the patient on a hanger so the liquid flows to the patient by means of gravity. However, such bottles are heavy and bulky. They are difficult to handle and subject to breakage. As a result, it has become more desirable in recent years to store such liquids in and administer such liquids from deformable plastic containers. These containers are usually formed of a plastic film, such as a polyvinylchloride film, and usually are equipped with ancillary tubes to adapt them to the particular purpose for which they are intended.

Recently it has been found advantageous to administer such liquids under pressure. Although a number of arrangements for supplying liquids under pressure have been proposed, many have not gained any commercial acceptance.

In accordance with one such proposal, a container comprises a first deformable bag for storing a liquid. This first bag is located within a second deformable bag that can be pressurized internally by a gas that is generated within the second bag. In another embodiment, the second bag is located within the first bag. When the gas is produced, the volume of the second bag increases and causes the volume of the first bag to decrease thereby dispensing the liquid under pressure. The expenses attendant with the manufacture of these concentric bags and the pressurization device that must be located in each container plus the problems of keeping these containers sterile apparently has lead to its lack of use in surgical procedures.

Similar concentric bags with an externally located pressurization device have been proposed. In one, a two-chamber container includes an inner collapsible liquid container and an outer container. Appropriate inlet and outlet means enable air to be pumped into the outer bag and the parenteral or the liquid to be stored in and dispensed from the inner bag. A reverse arrangement has also been proposed in which the air bag is dispoed inside the liquid bag. In either arrangement, the air bag is inflated to force the liquid out of the liquid bag under pressure.

Problems have been encountered with these bags, however, because the liquid bag tends to collapse and trap liquid; so the container with the trapped liquid must be thrown away before the liquid is completely used. Various solutions have been proposed. In one, the liquid chamber is centered in the air-chamber by means of flexible connecting stays. Alternatively, tubes are inserted into the liquid bag or the bag is constructed with special ribs that thereby prevent either premature closure of the bag or the entrapment of any liquid in the bag. Again, however, these special construction features tend to increase the overall costs of the bag. These containers have also not gained acceptance for use during surgical procedures.

In accordance with another approach, a container comprises juxtaposed chambers, rather than concentric bags. In one, three membranes are sealed about their peripheries to define juxtaposed liquid and pressure chambers. The container is then placed in a cardboard enclosure. When the pressure chamber is pressurized by some external means, the cardboard enclosure restricts any overall enlargement of the container. Thus, the center membrane displaces into the liquid chamber and forces the liquid out under pressure. These and other similar devices that contain juxtaposed chambers are also somewhat complex to manufacture because they are not readily produceable. This feature, as well as the need for various ancillary devices to overcome some of the foregoing problems encountered during administration of liquids, increases costs. Moreover, the need for ancillary devices, such as the foregoing cardboard enclosure, make it more difficult to handle these containers during surgical procedures.

Another possible reason for a lack of use of the prior containers during surgical procedures lies in the medical problems that can occur if the central membrane in a container having the juxtaposed chambers ruptures. If the membrane ruptures, air under pressure is admitted into the liquid chamber. If the resulting air then passes into the patient during an intravenous administration of the liquid, an embolus can result. Thus, the accepted method for delivery of liquids under pressure is to place a single chamber container with liquid into a blood pressure or other type of pressure cuff. The cuff is then inflated and contracts on the container. These pressure cuffs are cumbersome and difficult to handle. Moreover, they are difficult to sterilize. However, even with these drawbacks, the use of a pressure cuff and separate container is really the only method for delivering liquids under pressure that is widely accepted by the medical profession.

Therefore, it is an object of this invention to provide a liquid container for use in the administration of liquids to patients under pressure.

Another object of this invention is to provide a liquid container that reduces the risks of administering a liquid under pressure to a patient.

Another object of this invention is to provide a container for use as part of a pressurized liquid delivery system that is readily sterilizable.

Still another object of this invention is to provide a container for administering liquid under pressure that is easy and relatively inexpensive to manufacture.

SUMMARY

In accordance with one aspect of this invention, my container comprises three sheets of flexible material. The second sheet is shorter than the first and third sheets. One end of the second sheet is sealed to an intermediate portion of the first sheet and the co-extensive peripheral portions of all three sheets are then sealed together thereby to form a pressure chamber between the first and second sheets and a liquid chamber that is defined by the second and third sheets and a portion of the first sheet. Various fluids conduits are also positioned to provide passages to the liquid and pressure chambers.

In accordance with another aspect of this invention, a fourth sheet, that is substantially co-extensive with the second sheet, is inserted between the second and third sheets. However, the space between the second and fourth sheets is vented to atmosphere. If any gas should escape through the second sheet from the pressure chamber, it passes immediately to the atmosphere through this venting chamber and will not pass into the liquid.

This invention is pointed out with particularity in the appended claims. The above and further objects and advantages of this invention can be better understood by referring to the following detailed description taken in conjunction with the accompanying drawings.

BRIEF DESCRIPTION OF THE DRAWINGS

FIG. 2 is an elevation of a two-chamber container constructed in accordance with my invention;

FIGS. 3A and 3B are sections of the two-chamber bag shown in FIG. 2 and taken along lines 3A—3A and 3B—3B, respectively;

FIG. 4 is an elevation of a three-chamber container constructed in accordance with my invention; and FIGS. 5A and 5B are sections of the three-chamber bag shown in FIG. 4 and taken along lines 5A—5A and 5B—5B respectively.

DESCRIPTION OF AN ILLUSTRATIVE EMBODIMENT

Figure 1:
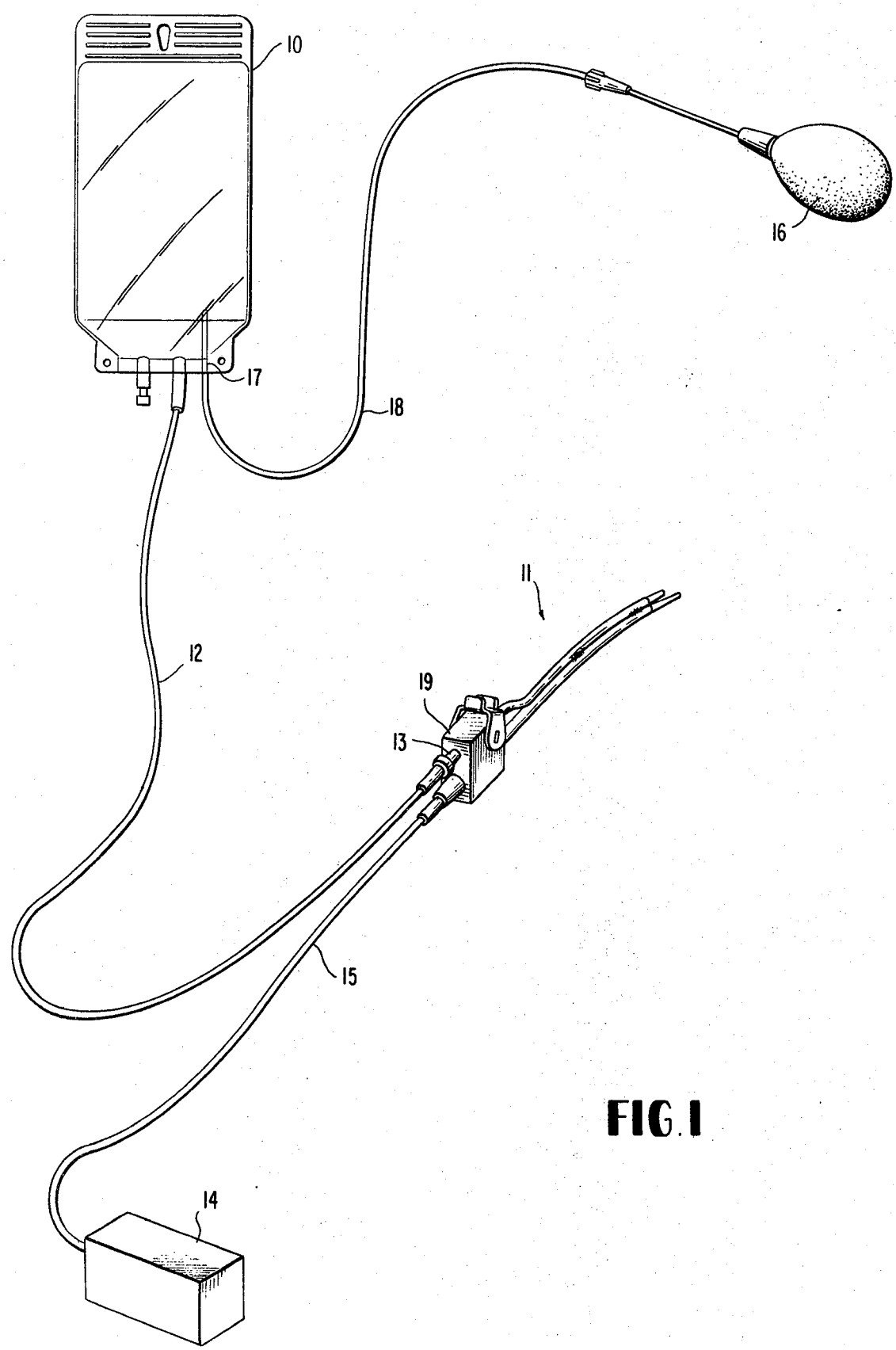
FIG. 1 is a perspective view of a suction-irrigator that can be used with a pressurized supply of a liquid delivered from a container constructed in accordance with my invention.

Referring to FIG. 1, a container 10 constructed in accordance with my invention is provided for delivering liquid under pressure to a suction-irrigator 11 through an integrally dispensing tube 12 that terminates in a standard male intravenous fitting 13. Suction is provided by a standard suction pump 14 that connects to the suction-irrigator 11 through a hose 15. In order to supply the liquid in the container 10 under pressure, a standard pressure bulb 16 connects to a pressure inlet port 17 in the container 10 by means of a hose 18. In use, the bulb 16 is pumped to pressurize a pressure chamber in the container which then places liquid in a liquid chamber in the container 10 under pressure. In this specific application, a valve 19 in the suction-irrigator 11 controls the flow of liquid under pressure. It will be apparent, especially from the following discussion, that the container 10 can be used in a wide variety of applications ranging from the external application of an irrigating solution from the apparatus shown in FIG. 1 to the intravenous administration of parenteral fluids and blood transfusions.

Referring to FIG. 2, a two-chamber container 20, constructed in accordance with my invention, is adapted for use in the administration of various fluids under pressure. It is characterized by having a handle section 21, a central chamber section 22 with liquid and pressure chambers and a conduit-holding section 23 that supports a filler port 24, an elongated dispensing tube 25 that terminates in a standard male intravenous fitting that is used in the dispensing of the liquid and a pressure line 26 that contains a female fitting for a standard intravenous fitting from a pressurized supply. The filler port 24 and dispensing tube 25 constitute conduits that communicate with the liquid chamber in the central chamber section 22. Normally the liquid chamber is filled with a saline solution through the filler port 24 which then is sealed with a membrane that can be punctured by a hypodermic needle in order to enable introduction of various medications to the saline solution as necessary. The pressure conduit 26, on the other hand, passes into the pressure chamber and serves as the pressure port 17 shown in FIG. 1 that enables the entire bag to be pressurized.

In use, a filled container 20 can be hung by means of an opening 27 in the handle section 21 on a conventional hanger or positioned in any other location relative to the patient. Some device, such as the pressure bulb 16 in FIG. 1 or other regulated pressure supply, is then attached to the pressure conduit 26 thereby to pressurize the bag while the administration device, such as the suction-irrigator in FIG. 1 is connected to the dispensing tube 25.

The simplicity of construction of the container 20 in FIG. 2 is more clearly shown in FIGS. 3A and 3B. More specifically, the container 20 comprises three plastic sheets 30, 31 and 32. Sheets 30 and 32 are conveniently formed of a polyvinylchloride or polyurethane sheet in the order of 10 mils thick and are of the same size. Sheet 31 is formed of a like material in the order of 5 mils thick. It has the same width as sheets 30 and 32 but is shorter. In accordance with one such procedure, the pressure tube 26 initially is positioned and tacked to it by heating or other known procedures. Next, sheet 31 is positioned on sheet 32 so that the portions that will form the handle section 21 (ends 31A and 32A of sheets 31 and 32) are even. Sheet 31 therefore terminates at a position 33 that is short of the end of sheet 32, but that overlies the pressure tube 26. The two sheets are then heat-sealed along the edge 33 and around the pressure conduit 26 without closing it. Next, the filler port 24 and dispensing tube 25 are positioned and tacked to the sheet 32. The sheet 30 then is placed on top of this assembly and the entire periphery of sheets 30 and 32 are bonded together. This bonding operation also seals the sheet 31 between sheets 30 and 32 along sides 34 and 35 shown in FIG. 2 and throughout the entire handle section. Next, the opening 27 in FIG. 2 is formed by heat stamping or other conventional steps.

The resulting container 20 has two chambers: a pressure chamber 36 and a liquid chamber 37 as most clearly shown in FIG. 3A. As the sheet 31 is thinner than sheets 30 and 32, any pressurization of the chamber 36 forces the wall 31 into the chamber 37. Thus, the sheet 31 acts as a piston or follower means as it pushes liquid from the liquid chamber 37 and takes up void space that is produced as liquid leaves the chamber 37. No external enclosures are required to prevent deformation of the outer walls 30 and 32. Moreover, it has been found that the liquid 37 chamber does not close prematurely and trap liquids, apparently because this construction prevents a complete collapse of the wall 31 onto the entire surface of the sheet 30.

It will also be apparent that the foregoing outline of construction steps describes a relatively simple manufacturing process. One reason is that only two elements or integral assemblies are handled at any one time. Also, only one sealing operation is performed on any specific portion of the bag at any given time so resealing operations, which sometimes actually cause poor sealing, are eliminated.

The two-chamber container shown in FIGS. 2, 3A and 3B is particularly advantageous for the external administration of fluids under pressure. Whenever it is necessary to protect against the introduction of an air embolus, the container shown in FIG. 2 can be modified along the lines shown in FIGS. 4, 5A and 5B. FIG. 4 shows one application of such a container that is constructed in accordance with another aspect of this invention. It is specifically adapted for use as a transfer pack for receiving blood from a donor and for dispensing blood to the recepient. This transfer container 40 contains a handle section 41, a central chamber section 42 including a liquid chamber and a pressure chamber and a conduit holding section 43. There are four connections to the transfer container 40 shown in FIG. 4. A filler tube 44 is used during a blood donation step and conveys blood from the donor into the liquid chamber in the portion 42. Once the donation has been completed, the filler tube 44 is sealed. Two sterile dispensing ports 45 and 46 are also provided. Such ports and their attendant sterilizing covers are well known. In accordance with this invention, however, there is also added to the transfer pack 40 a pressurizing tube 47 that is adapted for connection through a standard intravenous fitting 50 to an intravenous connection from an external manual pressure pump or automatic pressure regulating unit.

In accordance with this aspect of the invention, my container 40 is composed of four sheets of plastic material, these sheets being designated by reference numerals 51, 52, 53 and 54 in FIGS. 5A and 5B. The container 40 can be manufactured using similar steps as outlines with respect to the two-chamber container. More specifically, the pressure tube 47 is tacked to a sheet 54. Then the sheet 53, which is shorter than the sheet 54, is sealed along a line 55 to the sheet 54. Next, the sheet 52 is affixed to the sheet 54 at a point 56, the sheet 52 being slightly longer than the sheet 53. The various tubes 44, 45 and 46 are tacked to the free end of the sheet 54. Then the sheet 51, having the same area as sheet 54, is sealed to the assembly about its periphery thereby to produce three chambers 60, 61 and 62. Chamber 60 constitutes the liquid chamber for storing blood or like liquids while chamber 62 constitutes the pressure chamber.

During the construction of this container 40, however, the sealing operation is controlled so that the area in the handle section 41, beneath the opening 65 and designated by reference numeral 66 is not sealed between the sheets 52 and 53. As a result, the chamber 61 is vented to the atmosphere through the area 66 and the opening 65. Thus, if the membrane 53 were to rupture while the chamber 62 was pressurized, the resulting air would merely vent to the atmosphere. It would not pass through the membrane 52 thereby to form a pressurized air embolus in the blood or other liquid in the liquid chamber 60.

There are described two specific embodiments of my invention; namely, a two-chamber container and a three-chamber container. It will be apparent that there are many embodiments of this invention which may include additional elements. For example, in some embodiments it will be advantageous to provide an air leak sensing means, such as a whistle, that can be located in the area 66, to call attention to any malfunction from the bag in FIG. 4. It may also be desirable in some applications to provide some means for limiting the venting of the air from the container. In other arrangements, different materials may be utilized. We have described the invention in terms of polyvinylchloride or polyurethane sheets. On the other hand, the materials used for the sheets that form the liquid chamber might be chosen primarily for their compatability with a particular physiological liquid. In the three-chamber embodiment shown in FIG. 5A, the sheet 53 does not contact the liquid. It could be selected from a number of materials based upon its flex life without excessive regard to its physiological characteristics. Thus, the container shown in FIG. 4 enables materials to be selected on the basis of their properties for a particular function and eliminates the need for compromises which might otherwise be required.

It will be apparent that my invention can be utilized in a number of embodiments that vary from the specifically disclosed containers. These variations can be used with the attainment of some or all of the advantages that the specifically disclosed containers provide. Therefore, it is the intent of the appended claims to cover all such variations and modifications as come within the true spirit and scope of this invention.

What I claim as new and desire to secure by Letters Patent of the United States is:

1. A pressure infusion chamber for administering parenteral liquids into a patient comprising:
   A. first and second outer wall members of a flexible material,
   B. a first intermediate, flexible wall member interposed between said first and second outer wall members in a peripherally sealed relationship,
   C. a second intermediate, flexible wall member interposed between said first intermediate member and one of said outer wall members,
   D. said first and second intermediate wall members dividing said container into three separate chambers which include a fluid pressure chamber, a parenteral liquid infusion chamber and an intermediate chamber separating the aforesaid chambers,
   E. first and second port means connected to said fluid pressure chamber and said parenteral fluid chamber respectively for providing fluid passages into said chambers, and
   F. venting port means communicating with said intermediate chamber formed by said intermediate wall members whereby when said fluid pressure chamber is expanded under pressure, said parenteral liquid chamber is compressed thereby infusing parenteral liquid to a patient through said liquid port means, said vented intermediate chamber serving to prevent introduction of air or fluid into the patient in the event of rupture of said pressure chamber.

2. A container for dispensing liquid under pressure, said container comprising:
   A. a first sheet of flexible material having an outer periphery;
   B. a second sheet of flexible material having an outer periphery, said periphery being bonded to said first sheet in a sealing relationship and said second sheet terminating, at one portion of its perimeter, short of the periphery of said first sheet;
   C. a third sheet of flexible material having an outer periphery, the peripheries of said first and third sheets and coextensive portions of the periphery of said second sheet being joined in a sealing relationship, said first and third sheets wholly enclosing said second sheet, and wherein said first and second sheets define a first chamber and said first, second and third sheets define a second chamber;
   D. first conduit means positioned in the joint or seam between said second sheet perimeter portion and said first sheet for providing a passage to said first chamber and
   E. second conduit means positioned in the joint or seam between said first and third sheets outboard of said perimeter portion.

3. A container as recited in claim 2 wherein said second sheet is substantially thinner than said first and third sheets.

4. A container as recited in claim 2 wherein a portion of the perimeter of said second sheet is bonded between portions of the peripheries of said first and third sheets to form a handle section of said container.

5. A container as recited in claim 3 wherein the said second sheet is formed of a non-extensible organic polymer film from 2 to 5 mils thick and wherein said first and third sheets are formed of a non-extensible organic polymer film from 6 to 12 mils thick and wherein said second sheet is not more than about 60% of the thickness of either of said first and third sheets.

6. A container for dispensing liquid under pressure, said container comprising:
   A. a pair of co-extensive outer sheets having an outer periphery and formed of flexible material,
   B. an intermediate sheet having an outer periphery and being formed of a flexible material, said intermediate sheet being disposed between said pair of outer sheets, one portion of said periphery of said intermediate sheet being joined to one of said outer sheets in a sealing relationship at a position that is displaced from the periphery thereof, said sheets being joined in a sealing relationship about the outer periphery of the pair of the outer sheets and coextensive portions of said periphery of said intermediate sheet, and
   C. first and second conduit means extending through the joint or seam between said outer sheets one of said conduit means only also extending through the joint or seam between the displaced portion of the intermediate sheet periphery and said one outer sheet for providing independent access to chambers formed between said counterfacing surfaces of said sheets.

7. A container for dispensing liquid under pressure, said container comprising:
   A. a first sheet of flexible material having an outer periphery;
   B. a second sheet of flexible material having an outer periphery, said periphery being bonded to said first sheet in a sealing relationship and said second sheet terminating, at one portion of its perimeter, short of the periphery of said first sheet;
   C. a third sheet of flexible material having an outer periphery, the peripheries of said first and third sheets and coextensive portions of the periphery of said second sheet being joined in a sealing relationship, said first and third sheets wholly enclosing said second sheet, and wherein said first and second sheets define a first chamber and said first, second and third sheets define a second chamber;
   D. first and second conduit means for providing passages to said first and second chambers, respectively, and
   E. a fourth sheet of flexible material, said fourth sheet being sealed about its periphery to said first sheet, and particularly at:
      (i) a position intermediate
         (a) that wherein said first sheet is sealed to one portion of the perimeter of said third sheet, and
         (b) that wherein said first conduit means enters said first chamber, and
      (ii) into said handle portion of said container and wherein a conduit means is provided heading outside of said container from a chamber formed by said second and fourth sheets.

8. A container for dispensing liquid under pressure, said container comprising:
   A. first and second outer wall members of a flexible material,
   B. an intermediate wall member of flexible material joined to said first and second outer wall members in a sealing relationship wherein said first outer wall member and said intermediate wall member define a first chamber, and said first and second outer wall members and said intermediate wall member define a second chamber,
   C. first and second means connected to said first and second outer wall members respectively for providing fluid passages to said first and second chambers,
   D. a second intermediate wall member of flexible material disposed between said first intermediate wall member and said second outer wall member, said first and second intermediate wall members defining an intermediate chamber and said second intermediate and outer wall members defining a fluid chamber, and
   E. venting means communicating with said intermediate chamber.

9. A container as recited in claim 8 wherein said immediate wall member is formed of a material that is substantially thinner than the material of said first and second outer wall members.

10. A container for dispensing liquid under pressure, said container comprising:
   A. a pair of co-extensive outer sheets having an outer periphery and formed of flexible material,
   B. an intermediate sheet having an outer periphery and being formed of a flexible material, said intermediate sheet being disposed between said pair of outer sheets, one portion of said periphery of said intermediate sheet being joined to one of said outer sheets in a sealing relationship at a position that is displaced from the periphery thereof, said sheets being joined in a sealing relationship about the outer periphery of the pair of the outer sheets and coextensive portions of said periphery of said intermediate sheet,
   C. means connected to said outer sheets for providing independent access to chambers formed between said counterfacing surfaces of said sheets,
   D. a second intermediate sheet having an outer periphery and being formed of a flexible material, said second intermediate sheet being disposed between said first intermediate sheet and the other of said pair of coextensive outer sheets, one portion of said periphery of said second intermediate sheet being joined to said one outer sheet in a sealing relationship at a position that is between the periphery thereof and said one portion of said first intermediate sheet, said second intermediate sheet being joined in a sealing relationship about the remaining portions of the outer periphery thereof with the pair of outer sheets and coextensive portions of the first intermediate sheet thereby to form three chambers, and
   E. venting means communicating with the chamber between said first and second intermediate sheets.

* * * * *